United States Patent
Lin et al.

(10) Patent No.: US 12,233,417 B2
(45) Date of Patent: Feb. 25, 2025

(54) MICROFLUIDIC CHIP AND MICROFLUIDIC DEVICE FOR PHYSICOCHEMICALLY TREATING SINGLE CELL, AND METHOD FOR PHYSICOCHEMICALLY TREATING SINGLE CELL BY USING MICROFLUIDIC CHIP AND MICROFLUIDIC DEVICE

(71) Applicant: SHENZHEN VITAVITRO BIOTECH CO., LTD., Shenzhen (CN)

(72) Inventors: Xiaozhen Lin, Shenzhen (CN); Jie Wu, Shenzhen (CN); Yanjing Fang, Shenzhen (CN)

(73) Assignee: Shenzhen Vitavitro Biotech Co., Ltd., Shenzhen (CN)

( * ) Notice: Subject to any disclaimer, the term of this patent is extended or adjusted under 35 U.S.C. 154(b) by 659 days.

(21) Appl. No.: 16/973,555

(22) PCT Filed: Jul. 16, 2018

(86) PCT No.: PCT/CN2018/095750
§ 371 (c)(1),
(2) Date: Dec. 9, 2020

(87) PCT Pub. No.: WO2019/237449
PCT Pub. Date: Dec. 19, 2019

(65) Prior Publication Data
US 2021/0245156 A1 Aug. 12, 2021

(30) Foreign Application Priority Data
Jun. 12, 2018 (CN) .................. 201810598384.X

(51) Int. Cl.
*B01L 3/00* (2006.01)
*C12M 1/00* (2006.01)
*C12M 1/42* (2006.01)

(52) U.S. Cl.
CPC ....... *B01L 3/502738* (2013.01); *C12M 35/08* (2013.01); *C12M 47/04* (2013.01);
(Continued)

(58) Field of Classification Search
CPC ............ H01J 29/025; B01L 2300/0816; B01L 2300/0867; B01L 2400/049;
(Continued)

(56) References Cited

U.S. PATENT DOCUMENTS

| | | | |
|---|---|---|---|
| 2012/0270312 A1* | 10/2012 | Ericsson | C12N 1/02 435/325 |
| 2013/0081757 A1* | 4/2013 | Hung | C12M 23/12 156/292 |

(Continued)

FOREIGN PATENT DOCUMENTS

| | | | | |
|---|---|---|---|---|
| CN | 106669873 A | * | 5/2017 | .......... B01F 13/0064 |
| CN | 108102877 A | * | 6/2018 | ............ C12M 23/16 |

OTHER PUBLICATIONS

Lin at al ("A negative-pressure-driven microfluidic chip for the rapid detection of a bladder cancer biomarker in urine using bead-based enzyme-linked immunosorbent assay"). Biomicrofluidics 7, 024103 (Year: 2013).*

(Continued)

*Primary Examiner* — Jennifer Wecker
*Assistant Examiner* — Jonathan Bortoli
(74) *Attorney, Agent, or Firm* — Davis Wright Tremaine LLP

(57) ABSTRACT

Provided is a microfluidic chip for physicochemically treating a single cell whose diameter is 50-400 micrometers. The body of the microfluidic chip comprises a fluidic layer, a pneumatic layer, and an elastic film sandwiched between the fluidic layer and the pneumatic layer; the fluidic layer comprises a switch-back single cell treating and retrieving (Continued)

channel, a first reagent inflow channel, a second reagent inflow channel, a reagent mixing channel, a third reagent inflow channel, a backwash channel, and a negative pressure and waste liquid sharing channel; the pneumatic layer comprises a pneumatic micro-valve group for controlling the opening and closing of each channel in the fluidic layer; the first reagent inflow channel and the second reagent inflow channel are separately connected with the inlet of the reagent mixing channel; the reagent mixing channel, the third reagent inflow channel, the backwash channel, and the negative pressure and waste liquid sharing channel are separately connected with the switch-back single cell treating and retrieving channel; and the third reagent inflow channel and the backwash channel are separately independent channels or share one channel. Also provided is a microfluidic device comprising the microfluidic chip and a method for physicochemically treating a single cell by using the microfluidic chip and the microfluidic device.

18 Claims, 4 Drawing Sheets

(52) U.S. Cl.
CPC ............... *B01L 2300/0816* (2013.01); *B01L 2300/0867* (2013.01); *B01L 2400/049* (2013.01); *B01L 2400/0622* (2013.01)

(58) Field of Classification Search
CPC ....... B01L 2400/0622; B01L 3/502738; B01L 3/502753; B01L 3/502761; C12M 21/06; C12M 23/16; C12M 35/08; C12M 47/04; C12M 41/36; C12N 5/0603; C12N 5/0609

See application file for complete search history.

(56) References Cited

U.S. PATENT DOCUMENTS

| | | | |
|---|---|---|---|
| 2014/0194313 A1* | 7/2014 | Craighead | C12Q 1/6806 422/534 |
| 2014/0322101 A1* | 10/2014 | Saito | G01N 1/10 422/509 |
| 2015/0377861 A1* | 12/2015 | Pant | C12M 23/34 435/395 |
| 2016/0016140 A1* | 1/2016 | Jovanovich | B01L 3/502738 506/40 |

OTHER PUBLICATIONS

Kuswandi et al ("Optical sensing systems for microfluidic devices: A review"). Kuswandi et al Optical sensing systems for microfluidic devices: A review, Analytica Chimica Acta, vol. 601, Issue 2, 2007, pp. 141-155, ISSN 0003-2670, (Year: 2007).*
Hsiao et al ("Cytotoxicity analysis of water disinfection byproducts with a micro-pillar microfluidic device") Lab Chip, 2012, 12, 3891-3900 (Year: 2012).*
CN-106669873-A translation (Year: 2017).*

* cited by examiner

MICROFLUIDIC CHIP AND MICROFLUIDIC DEVICE FOR PHYSICOCHEMICALLY TREATING SINGLE CELL, AND METHOD FOR PHYSICOCHEMICALLY TREATING SINGLE CELL BY USING MICROFLUIDIC CHIP AND MICROFLUIDIC DEVICE

CROSS-REFERENCE TO RELATED APPLICATIONS

The present application is a U.S. National Stage entry under 35 U.S.C. § 371 of International Application No. PCT/CN2018/095750, filed on Jul. 16, 2018, designating the United States of America and published in Chinese on Dec. 19, 2019, which in turn claims priority to Chinese Application No. 201810598384.X, filed on Jun. 12, 2018, each of which is hereby incorporated by reference in its entirety.

Microfluidic Chip and Microfluidic Device for Physicochemically Treating Single Cell, and Method for Physicochemically Treating Single Cell by Using Microfluidic Chip and Microfluidic Device

TECHNICAL FIELD

The invention relates to the microfluidic field, and in particular relates to a microfluidic chip or a microfluidic device for physicochemically treating a single cell, and a method for physicochemically treating a single cell by using the microfluidic chip or the microfluidic device.

BACKGROUND ART

With the development of biotechnology and the needs in aspects of biomedicine, human assisted reproduction, and breed-conservation-and-breeding of animal husbandry, the cell freeze-thaw technology has become a feasible method for preservation of cells and biological tissues after more than 60 years of development.

Among those needs, the cryopreservation of human oocytes is concerned mostly and has widest application prospect. The infertility rate in China has increased from 3% in 1992 to about 20% now, and the main medical way to solve infertility is the in vitro fertilization (IVF) technology. In 2009, there were a total of 138 IVF institutions in China. As of 2012, there were a total of 356 institutions approved to carry out the human assisted reproductive technology and a total of 17 sperm banks in China. Although the number of the institutions had doubled in just 3 years, an operation for IVF in first-tier cities had to queue for no-less-than half a year on average, which was a state where demands had exceeded supplies. One of the main reasons for this state is the low efficiency of the current cell cryopreservation technology.

For germ cells, commonly used cryoprotectants comprise permeable protectants, such as glycerol, propylene glycol, and dimethyl sulfoxide, which are low-molecular neutral substances. Those cryoprotectants hydrate in a solution, thereby increasing the viscosity of the solution and weakening the crystallization process of water molecules. The cryoprotectants also comprise impermeable protectants, such as sucrose, ethylene glycol, and albumin, that play a protective role by making the solution be in a supercooled state and reducing the concentration of a solute at a specific temperature.

With the vigorous development of the cell industry and the rapid growth of market demands in recent years, the limitations of traditional manual operation of cell cryopreservation have become increasingly obvious. Some industry giants have introduced cell factories and cryopreserving apparatuses. However, the operation of these apparatuses is still based on a traditional manual operation, which does not have the possibility to operate cells delicately.

At present, some microfluidic chips in the market have realized the automatic operation of cell freezing. However, the ability of such microfluidic chips for delicately operating cells is insufficient: not only is there a lack of a reliable cell capture structure, which leads to a risk of losing a single cell as a high-value oocyte, but also the precision of liquid flow speed regulation is insufficient, which in turn affects the processing effect of the automatic operation. Also, due to the lack of a micro-valve system, it is impossible to realize reliable cut-off between various fluidics.

SUMMARY OF THE INVENTION

The present application provides a microfluidic chip and a microfluidic device for physicochemically treating a single cell, and a method for physicochemically treating a single cell by using the microfluidic chip or the microfluidic device.

In the first aspect, the present application provides a microfluidic chip for physicochemically treating a single cell. The body of the microfluidic chip may comprise a fluidic layer, a pneumatic layer, and an elastic film sandwiched between the fluidic layer and the pneumatic layer. The fluidic layer may comprise a switch-back single cell treating and retrieving channel, a first reagent inflow channel, a second reagent inflow channel, a reagent mixing channel, a third reagent inflow channel, a backwash channel, and a negative pressure and waste liquid sharing channel; the pneumatic layer may comprise a pneumatic micro-valve group for controlling the opening and closing of each channel in the fluidic layer; wherein the first reagent inflow channel and the second reagent inflow channel can be separately connected with the inlet of the reagent mixing channel; the reagent mixing channel, the third reagent inflow channel, the backwash channel, and the negative pressure and waste liquid sharing channel can be separately communicated with the switch-back single cell treating and retrieving channel; and the third reagent inflow channel and the backwash channel can be separately independent channels or share one channel.

In an embodiment of the present invention, the switch-back single cell treating and retrieving channel may comprise a cell loading channel, a cell treating region and a cell retrieving channel, wherein the cell loading channel and the cell retrieving channel may connect with the cell treating region at the same position upstream of the cell treating region, so that the single cell can move along the channels in a switch-back manner in the process of loading, treating and retrieving.

In another embodiment of the present invention, the cell loading channel can be connected with a cell inlet, i.e., a world-to-chip interface, for connecting with an external cell loading device, and the cell retrieving channel can be connected with a cell retrieving hole, i.e., a chip-to-world interface, for retrieving the cell.

In an embodiment of the present invention, the cell loading device may comprise an upper cover, a bottle body, and a lower cover. The wider upper half part of the bottle body is used for holding cell-containing liquid, and the narrower lower half part of the bottle body is used for connecting with the microfluidic chip and transporting cell-containing liquid. The cell-containing liquid can be sucked into the fluidic layer as driven by negative pressure.

In an embodiment of the present invention, the cell retrieving hole may comprise a microwell placed at the end of the cell retrieving channel, wherein the microwell can be a circular microhole whose vertical depth is slightly deeper (for example, 30 to 100 microns deeper) than or consistent with that of the cell retrieving channel. Preferably, the cell retrieving hole further comprises an annularly arranged micropillar array surrounding the microwell.

In another embodiment of the present invention, micropillar arrays may be placed at the connections between each of the reagent mixing channel, the third reagent inflow channel, the backwash channel, the negative pressure and waste liquid sharing channel and the switch-back single cell treating and retrieving channel. Preferably, an arc-shape arranged micropillar array may be placed at the connection between the cell treating region and the negative pressure and waste liquid sharing channel.

In another embodiment of the present invention, the negative pressure and waste liquid sharing channel can be connected with an external negative pressure source in the process of cell loading and can be connected with a waste liquid reservoir in the process of cell treating and retrieving.

In another embodiment of the present invention, the pneumatic micro-valve group may comprise 6 pneumatic micro-valves, wherein the first reagent inflow channel, the second reagent inflow channel and the reagent mixing channel can share one pneumatic micro-valve (V1); the negative pressure and waste liquid sharing channel, the cell loading channel, and the cell retrieving channel can be each controlled by one pneumatic micro-valve (V5, V3, and V4); when the third reagent inflow channel and the backwash channel are separately independent channels, they can be each controlled by one pneumatic micro-valve (V2, V6); and when the third reagent inflow channel and the backwash channel share one channel, one pneumatic micro-valve (V2) controls the inflow of the third reagent, and the other pneumatic micro-valve (V6) realizes the switching between forward-washing and backwashing of the cell treating region.

In the second aspect, the present application provides an automatic microfluidic device for physicochemically treating a single cell, which may comprise the microfluidic chip according to the first aspect aforementioned, an air pressure generation and tuning module, a logic controlling circuit and an optical fiber sensing module.

In an embodiment, the optical fiber sensing module is used for monitoring the position of a cell, and the logic controlling circuit judges whether the cell reaches a designated position by reading a cell sensing signal in real-time and then judges whether to execute the next operation step.

In the third aspect, the present application provides a method for physicochemically treating a single cell by using the microfluidic chip mentioned in the first aspect or the microfluidic device mentioned in the second aspect, and the method may comprise:

(1) dripping a single cell into the cell loading device, and using negative pressure to suck the single cell into the chip;

(2) initiating the physicochemical treating process if an optical fiber sensing module detects the cell sensing signal when the cell is captured in a cell treating region: physicochemically treating the cell sequentially with a first reagent, a second reagent and a high-speed third reagent in different proportions by controlling the pneumatic micro-valve group; and (3) backwashing the cell into the cell retrieving channel with the third reagent after treatment, until the cell is captured at a microwell of a cell retrieving hole; continually discharging the redundant third reagent until the residual volume does not exceed 1 microliter, then opening the plug of the cell retrieving hole, and sucking the cell out by a special cell extraction tool to complete the retrieval.

In an embodiment, during the physicochemical treatment of the cell, the dosage rate of the first reagent to the second reagent can gradually change from 100:0 to 0:100 in gradients, and the flow rate of the third reagent can be 4-20 times of average flow rate of the first reagent or the second reagent.

Figure 1:
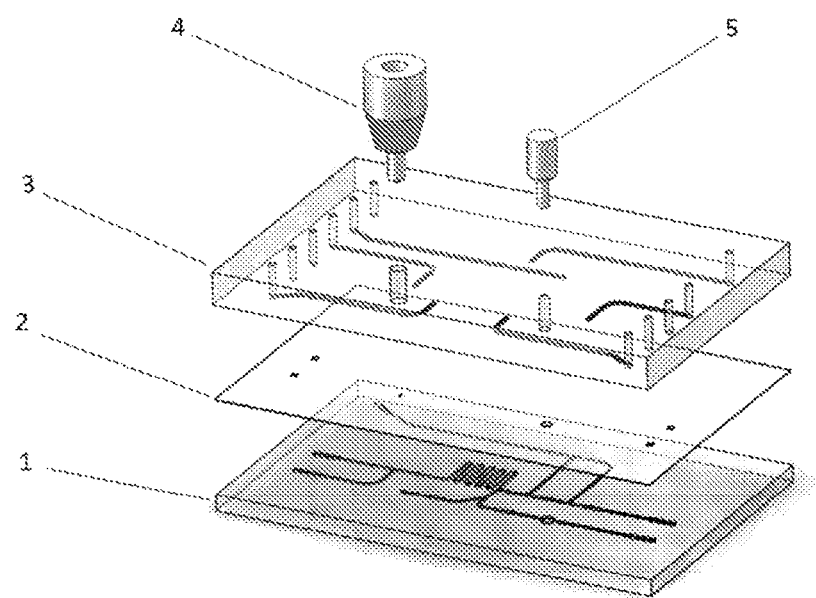
FIG. 1 is a schematic diagram about a three-layer structure of a microfluidic chip used for treating a switch-back single cell of the invention, comprising a cell loading device and a plug of a cell retrieving hole above the three-layer structure.

In the drawings, 1 represents a fluidic layer; 2 represents an elastic film; 3 represents a pneumatic layer; 4 represents a cell loading device; 101 represents a first reagent inflow channel; 102 represents a second reagent inflow channel; 103 represents a reagent mixing channel; 1041 represents a third reagent inflow channel; 1042 represents a backwash channel; 105 represents a negative pressure and waste liquid sharing channel; 106 represents a cell loading channel; 107 represents a cell treating region; 108 represents a cell retrieving channel; 109 represents a waste liquid reservoir; 110 represents a negative pressure pump; 111 represents a cell retrieving hole; V1-6 represent built-in pneumatic micro-valves; SV1-4 represent switching valves; CH1-6 represent pressure pump channels.

DETAILED DESCRIPTION OF EMBODIMENTS

The microfluidic chip of the invention is used for physicochemically treating a single cell whose diameter is 50-400 micrometers, especially treating a single germ cell. Due to the scarcity of the germ cell, the whole treatment process must ensure that the cell is intact, which makes the requirements of the microfluidic chip for treating such a germ cell substantially different from those for treating a large number of nondistinctive cells.

Specifically, on the basis of better controlling the treatment process before cell freezing and of realizing the automatic control in the whole process, the microfluidic chip of the invention can ensure that the cell is not subjected to any damage. As shown in FIG. 1, the body of the microfluidic chip of the invention may comprise a fluidic layer 1, a pneumatic layer 3, and an elastic film 2 sandwiched between the fluidic layer and the pneumatic layer. When a high-pressure gas is injected into a pneumatic controlling channel in the pneumatic layer 3, the elastic film 2 under the pneumatic controlling channel bends downward to squeeze a liquid flow channel under the elastic film; and when the high-pressure gas is removed, the elastic film 2 recovers. That is how the pneumatic micro-valve is controlled. This control method is well known in the microfluidic field. The pneumatic layer 3 may comprise a pneumatic micro-valve group for opening and closing each channel in the fluidic layer 1.

Figure 2A:
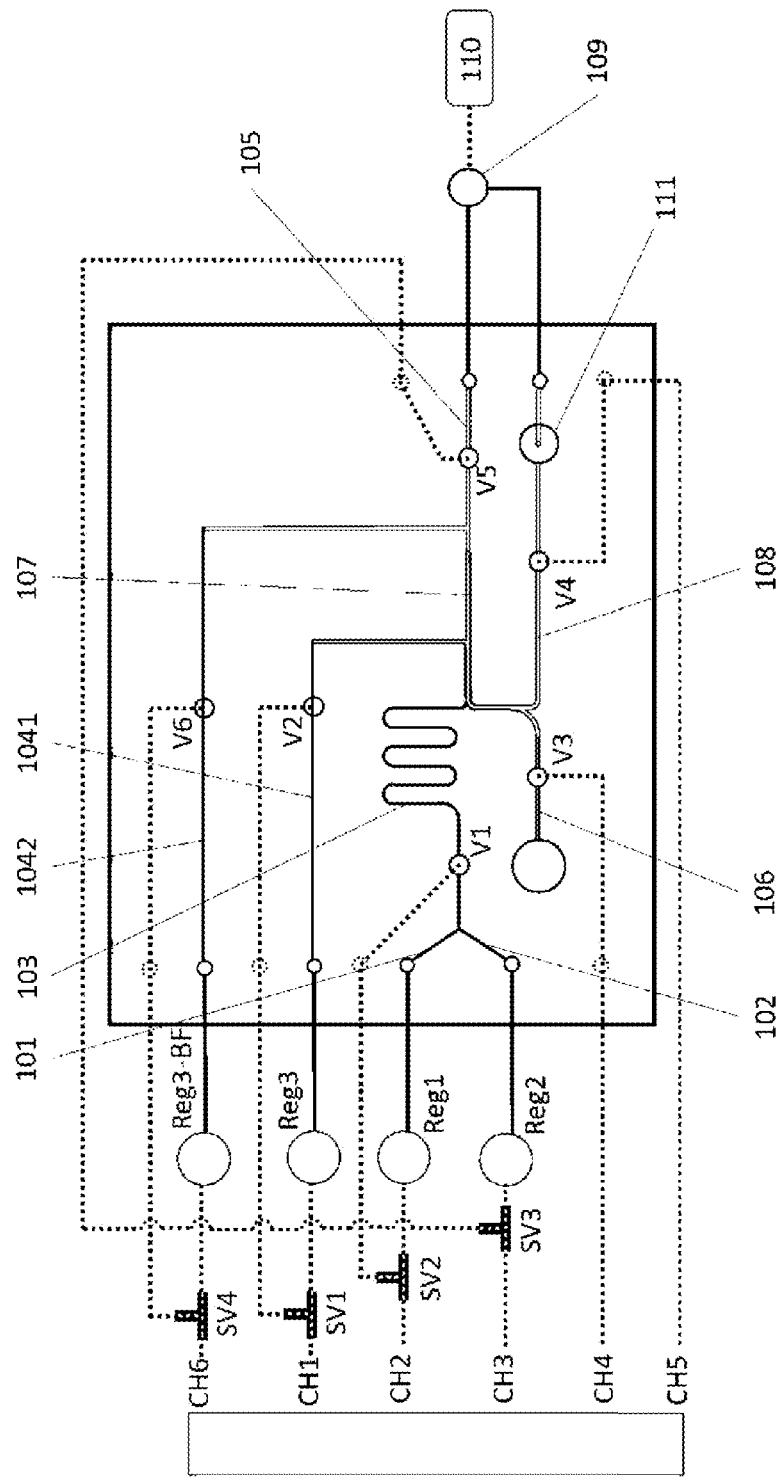
FIG. 2A is a schematic top view of the switch-back single cell treating chip according to an embodiment of the invention.

FIG. 2A is a schematic diagram of a body of the microfluidic chip. As shown in FIG. 2A, the fluidic layer 1 may comprise a switch-back single cell treating and retrieving channel, a first reagent inflow channel 101, a second reagent inflow channel 102, a reagent mixing channel 103, a third reagent inflow channel 1041, a backwash channel 1042, and a negative pressure and waste liquid sharing channel 105. The first reagent inflow channel 101 and the second reagent inflow channel 102 can be separately connected with the inlet of the reagent mixing channel 103; and the reagent mixing channel 103, the third reagent inflow channel 1041, the backwash channel 1042, and the negative pressure and waste liquid sharing channel 105 can be separately connected with the switch-back single cell treating and retrieving channel. Preferably, the inner diameter of the outlet of each of the reagent mixing channel 103, the third reagent inflow channel 1041, the backwash channel 1042, and the negative pressure and waste liquid sharing channel 105 can be smaller than the outer diameter of the cell, so that it can prevent the cell from flowing out of the outlets of these channels, in FIG. 2A, the third reagent inflow channel 1041, and the backwash channel 1042 are separately independent channels. At this time, the reagent for backwashing may be another reagent different from the third reagent, but it is preferable to use the third reagent.

The switch-back single cell treating and retrieving channel may comprise a cell loading channel 106, a cell treating region 107, and a cell retrieving channel 108, and the inner diameters of these channels should be larger than the outer diameter of the cell to avoid damage to the cell. The cell loading channel 106 and the cell retrieving channel 108 can be connected with the cell treating region 107 at the same position (see the shaded part in the figure) upstream of the cell treating region 107, so that a single cell can move along the channels in a switch-back manner in the processes of loading, treating and retrieving. The design of the switch-back channel of the invention can reduce the number of pressure channels and pneumatic micro-valves, thereby saving the manufacturing and treating costs of the chip. It is completely different from the circulating channel design, which only aims at capturing cells as adopted in the prior art.

The cell loading channel 106 can be connected to a cell inlet, i.e., a world-to-chip interface, and through the cell inlet, the microfluidic chip can be connected with an external cell loading device 4. As shown in FIG. 1, the cell loading device 4 is a dedicated apparatus specially designed for adapting to the microfluidic chip of the invention, comprises an upper cover, a bottle body, and a lower cover, and is used for containing a cell-containing liquid. The upper half part of the bottle body is wider, and the cell-containing liquid is mainly stored in this part. The lower half part of the bottle body is narrower and is used for connecting with the microfluidic chip and transporting the cell-containing liquid. When a cell needs to be loaded, the cell loading device 4 should be installed at the cell inlet on the microfluidic chip; then the upper cover should be removed, so that the cell-containing liquid can enter the fluidic layer 1 and flow when driven by a negative pressure air pump 110. The unique design of the world-to-chip interface of the invention, when combined with the negative pressure suction method, makes the seamless connection between a conventional laboratory cell operation and the microfluidic chip operation. Furthermore, this design of the world-to-chip interface of the invention allows the microliter-grade liquid to be directly dropwise-added and sucked, and the cell can be treated immediately upon acquiring, while the conventional cell loading method often uses a positive pressure to feed the liquid with a large number of cells into the chip through an external pipeline.

Figure 4:
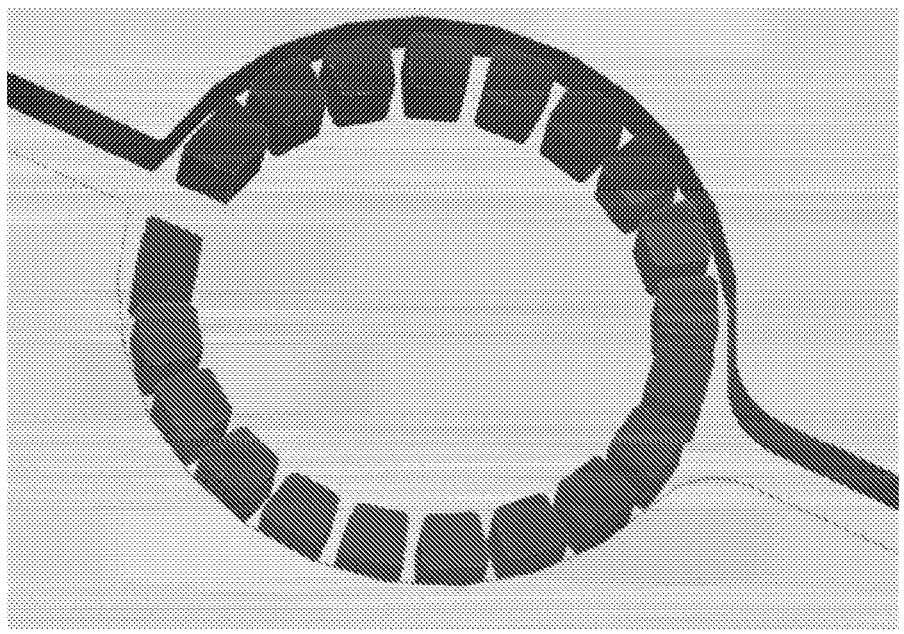
FIG. 4 is an enlarged schematic diagram of a cell retrieving hole, comprising a microwell and an annularly arranged micropillar array.

The cell retrieving channel 108 can be connected with the cell retrieving hole 111, i.e., a chip-to-world interface. The cell retrieving hole 111 may comprise a microwell placed at the end of the cell retrieving channel 108. As shown in FIG. 4, the microwell may be a circular microhole whose vertical depth is slightly more in-depth than or consistent with that of the cell retrieving channel 108. When the cell to be treated is heavy or has a low concentration in a solvent, there is a possibility of cell settling. At this time, preferably, the vertical depth of the microwell is 30 to 100 micrometers deeper than that of the cell retrieving channel 108. This specific range depends on the size of the cell to be treated. The larger the cell is, the deeper the vertical depth of the microwell is. After capturing a single cell, a trace reagent, such as the residual third reagent of no more than 1 microliter, is still needed to ensure that the cell can be extracted from the chip by a special cell extraction tool. In a preferred solution, the cell retrieving hole 111 may also comprise an annularly arranged micropillar array surrounding the microwell. The cell retrieving hole 111 is connected with one end of a hole passage which passes through the elastic film 2, and the pneumatic layer 3 upward from the fluidic layer 1, and the other end of the hole passage can be equipped with a cell retrieving hole plug 5. The unique design of the chip-to-world interface of the invention can efficiently separate the cell from the treating solution on the one hand, and realize the seamless connection with subsequent conventional laboratory cell operations on the other hand. This is fundamentally different from the conventional microfluidic chip for cell treating. The conventional microfluidic chip is often used for achieving purposes such as cell sorting, counting, culturing, or observing, and the cells will be discarded after relevant treatment. However, the microfluidic chip of the invention aims at high-value cells which are difficult to acquire and should not be discarded, and the cells must be restored at an intact state after the treatment.

The pneumatic micro-valve group in the pneumatic layer 3 may comprise 6 pneumatic micro-valves, which are embodied in FIG. 2 as follows: the first reagent inflow channel 101, the second reagent inflow channel 102, and the reagent mixing channel 103 share one pneumatic micro-valve V1, and the third reagent inflow channel 1041, the backwash channel 1042, the negative pressure and waste liquid sharing channel 105, the cell loading channel 106, and the cell retrieving channel 108 are each controlled by a pneumatic micro-valve (corresponding to V2, V6, V5, V3, and V4, respectively).

Figure 2B:
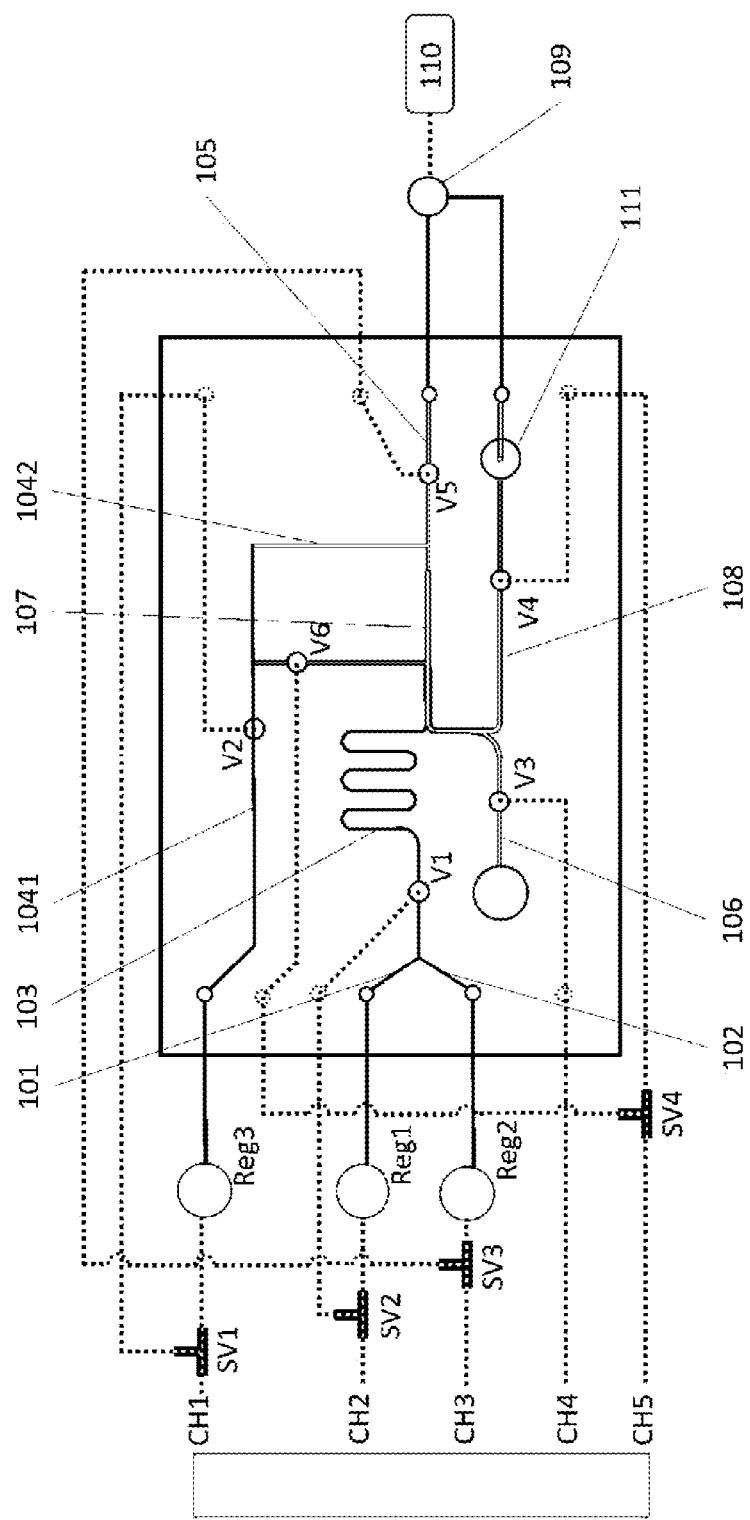
FIG. 2B is a schematic top view of the switch-back single cell treating chip according to another embodiment of the invention.

FIG. 2B shows another layout of the body of the microfluidic chip. It differs from FIG. 2A only in that the third reagent inflow channel 1041 and the backwash channel 1042 share one channel, specifically a partially shared channel. That is, after passing through the pneumatic micro-valve V2, the third reagent inflow channel 1041 continues to extend to and connects with the backwash channel 1042. In this case, the pneumatic micro-valve V2 is still used for controlling the inflow of the third reagent, while the other pneumatic micro-valve V6 is used for switching between forward-washing and backwashing of the cell treating region. Accordingly, both the third reagent backwash liquid reservoir (Reg3-BF) and an independent section of the backwash channel 1042 in FIG. 2A can be omitted.

Figure 3:
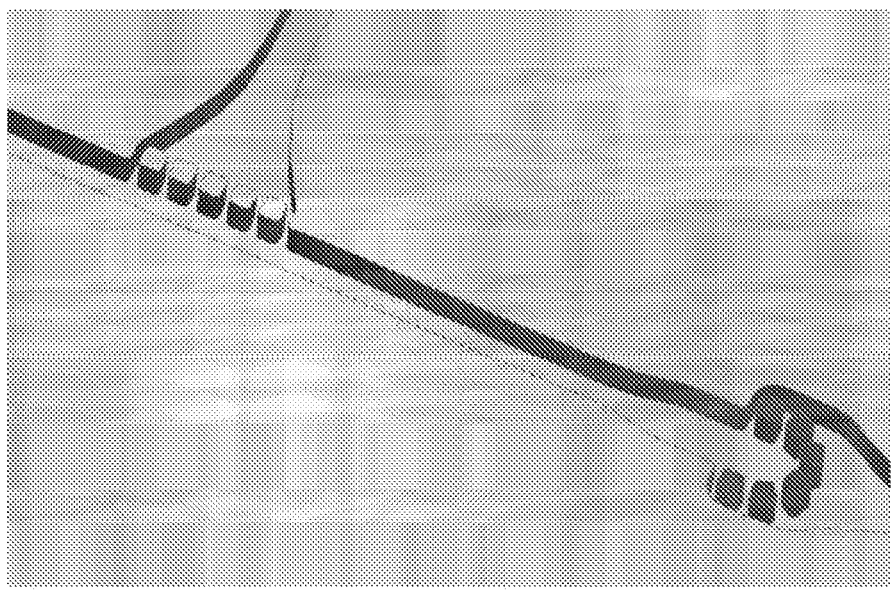
FIG. 3 shows a situation where micropillar arrays are placed at the connection between a cell treating region and each of a third reagent inflow channel and negative pressure and waste liquid sharing channel.

According to the invention, micropillar arrays may be placed at the connection between each of the reagent mixing channel 103, the third reagent inflow channel 1041, the backwash channel 1042, and the negative pressure and waste liquid sharing channel 105 and the switch-back single cell treating and retrieving channel, to prevent the cell from leaving the cell treating region 107. For example, FIG. 3 shows a situation where the micropillar arrays are placed at the connection between the cell treating region 107 of the switch-back single cell treating and retrieving channel. Each of the third reagent inflow channel and the negative pressure and waste liquid sharing channel 105, wherein preferably an arc-shape arranged micropillar array can be placed at the connection between the cell treating region 107 and the negative pressure and waste liquid sharing channel 105.

In the present invention, the shape of the micropillar can be selected from any one or a combination of a cylinder, a cuboid, a terrace, a cone, an open-type groove structure, and the like. The micropillar array comprises at least two micropillars, and a gap, which can block the single cell but allow liquid to pass through, is formed between adjacent micropillars. The micropillar array can be arranged in a shape of a straight line, an arc, a ring, etc., depending on the effect of blocking the cell, the possibility of damaging the cell, and the difficulty level of processing. The gap between the micropillars can be determined according to the specific size of the cell to be treated, and a drag of the liquid flow should be kept as small as possible while it can be ensured that the cell can be stuck. In a word, the size, number, and gap of the micropillars vary with the total width of the channels and are mainly explicitly determined according to the volume and diameter of the cell.

According to the invention, the negative pressure and waste liquid sharing channel 105 can be connected with an external negative pressure source 110 in the process of cell loading, and can be connected with a waste liquid reservoir 109 in the processes of cell treating and retrieving. Such a design effectively reduces the total number of channels in the chip and facilitates the processing of the chip.

The microfluidic chip of the invention can work with the air pressure generation and tuning module, the logic controlling circuit, and the optical fiber sensing module synergistically to form a microfluidic device, thereby realizing a full-automatic physicochemical treatment of the single cell. The air pressure generation and tuning module may comprise a gas source, a negative pressure pump 110, a pressure regulating valve, switching valves SV1-4, and a flowmeter. The optical fiber sensing module may comprise an optical fiber head and an optical fiber amplifier. The logic controlling circuit can automatically control the air supply pressure and the gear position of the switching valves by running program instructions, to control the liquid flow rate in the microfluidic chip, and the opening and closing of the pneumatic micro-valve; by reading a flow rate value in real-time, feeding it back and adjusting the air supply pressure, which ensures the stability of the liquid flow speed; by reading the optical fiber sensing signal in real-time to judge whether the cell reaches a designated position, then the circuit judges whether to execute the next step, thereby realizing an automatic treatment of the single cell. By adopting optical fiber sensing, the microfluidic device of the invention not only has high sensitivity but also does not need to build any sensor into the chip; and compared with other conventional sensing methods such as electrical impedance sensing, this non-invasive sensing method causes almost no damage to the cell.

The process of physicochemically treating a single cell by using the microfluidic chip or microfluidic device of the invention is described below. Specifically, the treatment method of the present invention can comprise the following steps:
  (1) dripping a single cell into the cell loading device 4 and using negative pressure to suck the single cell into the chip, after the pneumatic micro-valves V3 and V5 have opened and the pneumatic micro-valve V4 has closed;
  (2) initiating the physicochemical treatment process if the optical fiber sensing module detects the cell sensing's signal when the cell is captured in the cell treating region 107: after the pneumatic micro-valves V3 and V4 have closed and the pneumatic micro-valve V5 has opened, physicochemically treating the cell sequentially with a first reagent Reg1, a second reagent Reg2 and a high-speed third reagent Reg3 in different proportions by controlling pneumatic micro-valves V1 and V2; and
  (3) backwashing the cell into the cell retrieving channel 108 with the third reagent Reg3 after treatment, until the cell is captured at a microwell of a cell retrieving hole, after the pneumatic micro-valve V4 has opened and the pneumatic micro-valve V5 has closed; continually discharging the redundant third reagent until there is little reagent remained, opening the plug of the cell retrieving hole, and sucking the cell out by a special cell extraction tool to complete the retrieval. If the third reagent inflow channel 1041 and the backwash channel 1042 are separately independent channels, the third reagent Reg3 is driven to perform cell backwash after the pneumatic micro-valve V6 has opened and the pneumatic micro-valve V2 has closed (as shown in FIG. 2A); if the third reagent inflow channel 1041 and the backwash channel 1042 are partially shared (as shown in FIG. 2B), the third reagent Reg3 is driven to perform cell backwash after the pneumatic micro-valve V6 has closed and the pneumatic micro-valve V2 has opened.

Before the single cell is loaded in the step (1), the microfluidic chip can be pretreated, that is, washing the chip with the first reagent Reg1.

In the step (2), the physicochemical treatment process may specifically comprise: I. opening the pneumatic micro-valve V1 to drive the first reagent Reg1 into the chip; II. driving the second reagent Reg2 into the chip; III. changing the flow rate of Reg1 and Reg2 gradually, and washing the cell after their mixing has completed, wherein the rate of Reg1 to Reg2 may change from 100:0 to 0:100 in gradients gradually; and IV. closing the pneumatic micro-valve V1 while opening the pneumatic micro-valve V2, and driving the third reagent Reg3 to wash the cell, wherein the flow rate of the third reagent can be 4-20 times of the average flow rate of the first reagent or the second reagent, such as 120-600 microliters/minute, depending on the specific cell to be treated.

The essence of physicochemically treating the cell by these three reagents is to realize the replacement with intracellular substances, which is mainly driven by osmotic pressure. According to the invention, the first reagent Reg1 and the second reagent Reg2 treat the cell slowly and react with the cell slowly, wherein the dosage of Reg1 can be gradually reduced from 100% to 0 in gradients, whereas the dosage of Reg2 can be gradually increased from 0 to 100% in gradients. This gradient change of the flow rate of the first to second reagents is beneficial to ensure that the osmotic pressure inside and outside the cell are changed slowly. As shown in the following examples, for the treatment for a total duration of 15 minutes, the flow rate s of Reg1 to Reg2 can be controlled in gradients, as shown in the table below:

| Treatment duration (seconds) | 36 | 36 | 36 | 36 | 36 | 36 | 36 | 36 | 36 | 36 | 540 |
|---|---|---|---|---|---|---|---|---|---|---|---|
| The flow rate of Reg1 (microliter/minute) | 60 | 54 | 48 | 42 | 36 | 30 | 24 | 18 | 12 | 6 | 0 |
| The flow rate of Reg2 (microliter/minute) | 0 | 6 | 12 | 18 | 24 | 30 | 36 | 42 | 48 | 54 | 60 |

The main function of the third reagent Reg3 is to infiltrate the cell to replace water in the cell. As the time for treatment with Reg3 is short, it needs to process the treatment at a higher flow rate, such as 120 to 600 microliters/minute, i.e., treatment at a high rate.

According to the present invention, the main components of the first reagent Reg1 may be the M199 buffer, human serum albumin, etc. The main components of the second reagent Reg2 may be the M199 buffer, ethylene glycol, dimethyl sulfoxide, etc. The main components of the third reagent Reg3 may be the M199 buffer, ethylene glycol, dimethyl sulfoxide, sugar, etc.

The microfluidic chip, the microfluidic device, and the method for treating a single cell of the invention can coordinate with a germ cell freezing apparatus to realize a full-automatic and integrated operation with high stability and accurate control, thereby meeting the increasing industrial's demand. Furthermore, the invention can ensure that a capture rate of 100% is achieved while the cell is intact, which is of great significance to rare and precious germ cells, and is also helpful to improve and stabilize the survival rate of cells that have been cryopreserve-and-thawed.

EXAMPLES

Hereinafter, the invention will be explained in more detail by examples.

The microfluidic chip of the examples is used for treating human oocytes, bovine oocytes, or bovine embryos with a cell size of 120-150 microns, wherein the inner diameter of each channel is about 200 micrometers. The inner diameter of the end of the cell retrieving channel 108 gradually changes from 200 micrometers to 300 micrometers and then changes to the cell retrieving hole with an inner diameter of about 650 micrometers. The micropillar is a cuboid with a length, width, and height of 100 micrometers by 100 micrometers by 200 micrometers, and the gap between the micropillars is set at about 50 micrometers.

Example 1 A bovine embryo was treated with the microfluidic chip, as shown in FIG. 2A. The detailed operation process was as follows:

Step 1: washing the chip with a first reagent Reg1

The first reagent Reg1 was placed into the liquid reservoir (Reg3) at the inlet of the third reagent inflow channel 1041 and into the liquid reservoir (Reg3-BF) at the inlet of the backwash channel 1042. Then, the gas pressure-supplying direction of the gas switching valves SV1, SV2, SV3, and SV4 was adjusted to the direction of the fluidic (as shown by the black line in FIG. 2), while the negative pressure device was kept closed.

The pneumatic channel CH2 was pressurized, and the switching valve SV2 was switched to V1 position, and the built-in pneumatic micro-valve V1 was closed; the pneumatic channel CH4 was pressurized and the built-in pneumatic micro-valve V3 was closed; the pneumatic channels CH1 and CH6 were pressurized, and Reg1 was driven to wash the internal fluidic channel of the chip and was finally discharged into the waste liquid reservoir 109 outside the chip through the negative pressure and waste liquid sharing channel 105.

Step 2: Preparing a Cell Treatment Reagent

The reagents in the liquid reservoirs at the inlets of the first reagent inflow channel 101, the second reagent inflow channel 102, the third reagent inflow channel 1041, and the backwash channel 1042 were prepared, so that the reagents in the liquid reservoirs correspond to the numbering of the liquid reservoirs. The pneumatic channel CH1 was pressurized and the switching valve SV1 was switched to V2 position, and the built-in pneumatic micro-valve V2 was closed; the pneumatic channel CH6 was pressurized, and the switching valve SV4 was switched to V6 position, and the built-in pneumatic micro-valve V6 was closed; the pneumatic channel CH5 was pressurized and the built-in pneumatic micro-valve V4 was closed.

Step 3: Loading a Single Cell to be Treated

The cell loading device 4 was inserted into the cell inlet of the chip. The single cell to be treated was taken out of a culture dish and injected into the cell loading device 4 together with the accompanying culture medium. Pressurizing of CH4 was stopped, the built-in pneumatic micro-valve V3 was opened, and the negative pressure pump 110 was started so that the cell was sucked into the cell treating region 107 of the chip under the action of negative pressure. When the cell reached a designated position in the treating region, the optical fiber sensing module detected the cell and sent a signal to the logic controlling circuit, the logic controlling circuit then stopped the operation of the negative pressure pump. Then the pneumatic channel CH4 was pressurized, and the built-in pneumatic micro-valve V3 was closed.

Step 4: Treating the Cell

The switching valve SV2 was switched to the direction of the Reg1 liquid reservoir, the built-in pneumatic micro-valve V1 was opened, the pressure of the pneumatic channel CH2 was adjusted, and Reg1 was driven into the chip; the switching valve SV3 was switched to the direction of Reg2 liquid reservoir, the pressure of the pneumatic channel CH3 was adjusted, and the second reagent Reg2 was driven into the chip; the flow rate of Reg1 to Reg2 was gradually changed according to the following table, and the cell was washed after the mixing was completed.

| Treatment duration (seconds) | 36 | 36 | 36 | 36 | 36 | 36 | 36 | 36 | 36 | 36 | 540 |
|---|---|---|---|---|---|---|---|---|---|---|---|
| The flow rate of Reg1 (microliter/minute) | 60 | 54 | 48 | 42 | 36 | 30 | 24 | 18 | 12 | 6 | 0 |
| The flow rate of Reg2 (microliter/minute) | 0 | 6 | 12 | 18 | 24 | 30 | 36 | 42 | 48 | 54 | 60 |

The switching valve SV2 was switched to V1 position, and the built-in pneumatic micro-valve V1 was closed; the switching valve SV1 was switched to the direction of the third reagent Reg3 liquid reservoir, the built-in pneumatic micro-valve V2 was opened, the pressure of the pneumatic channel CH1 was adjusted, and Reg3 was driven to wash the cell, with the flow rate of Reg3 being about 300 microliters/minute.

The reagents Reg1-3 were injected into the chip in an orderly and gradient manner according to a predetermined design and reacted with the cell in the cell treating region 107 to meet the predetermined cell treating requirements.

In the process of cell treating, the operator could also pause and modify the treating parameters at any time according to a morphological observation result of the cell.

Step 5: Retrieving the Cell

The switching valve SV1 was switched to the V2 position, and the built-in pneumatic micro-valve V2 was closed; pressurizing of the pneumatic channel CH5 was stopped, and the built-in pneumatic micro-valve V4 was opened. The switching valve SV3 was switched to the V5 position, and the built-in pneumatic micro-valve V5 was closed. The switching valve SV4 was switched to the Reg3-BF position, the built-in pneumatic micro-valve V6 was opened, the pressure of the pneumatic channel CH6 was adjusted, and the third reagent Reg3 was driven to travel along the backwash channel 1042. At this time, the flow direction of Reg3 through the cell treating region 107 was changed from flowing from left to right in the fourth step to flowing from right to left, and the cell was further pushed into the cell retrieving hole.

Then, the input of Reg3 was stopped, and the subsequent gas flow entirely removed the reagent liquid around the cell. After evacuating the reagent, the cell retrieving hole plug was opened, and the treated cell was extracted with a straw or a strip, as the cell carrier.

Example 2

A human oocyte was treated with the microfluidic chip, as shown in FIG. 2B. The detailed operation process was as follows:

Step 1: Washing the Chip with a First Reagent Reg1

The first reagent Reg1 was placed into the liquid reservoir at the inlet of the third reagent inflow channel 1041. Then, the gas pressure-supplying direction of the gas switching valves SV1, SV2, and SV3 was adjusted to the direction of the fluidic (as shown by the black line in FIG. 2), while the negative pressure device was kept closed.

The pneumatic channel CH2 was pressurized and the switching valve SV2 was switched to V1 position, and the built-in pneumatic micro-valve V1 was closed; the pneumatic channel CH4 was pressurized and the built-in pneumatic micro-valve V3 was closed; the pneumatic channel CH1 was pressurized, and Reg1 was driven to wash the internal fluidic pipeline of the chip and was finally discharged into the waste liquid reservoir 109 outside the chip through the negative pressure and waste liquid sharing channel 105.

Step 2: Preparing a Cell Treatment Reagent

The reagents in the liquid reservoirs at the inlets of the first reagent inflow channel 101, the second reagent inflow channel 102, and the third reagent inflow channel 1041 were prepared, so that the reagents in the liquid reservoirs correspond to the numbering of the liquid reservoirs. The pneumatic channel CH1 was pressurized and the switching valve SV1 was switched to V2 position, and the built-in pneumatic micro-valve V2 was closed; the pneumatic channel CH5 was pressurized, and the switching valve SV4 was switched to V4 position, and the built-in pneumatic micro-valve V4 was closed.

Step 3: Loading a Single Cell to be Treated

The cell loading device 4 was inserted into the cell inlet of the chip. The single cell to be treated was taken out of a Petri dish and injected into the cell loading device 4 together with the accompanying culture liquid. The built-in pneumatic micro-valve V3 was opened, and the negative pressure pump 110 was started so that the cell was sucked into the cell treating region 107 of the chip under the action of negative pressure. When the cell reached a designated position in the treating region, the optical fiber sensing module detected the cell and sent a signal to the logic controlling circuit, the logic controlling circuit then stopped the operation of the negative pressure pump. Then the pneumatic channel CH4 was pressurized, and the built-in pneumatic micro-valve V3 was closed.

Step 4: Treating the Cell

The switching valve SV2 was switched to the direction of the Reg1 liquid reservoir, the built-in pneumatic micro-valve V1 was opened, the pressure of the pneumatic channel CH2 was adjusted, and Reg1 was driven into the chip; the switching valve SV3 was switched to the direction of the Reg2 liquid reservoir, the pressure of the pneumatic channel CH3 was adjusted, and the second reagent Reg2 was driven into the chip; the flow rate of Reg1 and Reg2 was gradually changed, and the cell was washed after the mixing was completed.

The switching valve SV2 was switched to V1 position, and the built-in pneumatic micro-valve V1 was closed; the switching valve SV1 was switched to the direction of the third reagent Reg3 liquid reservoir, the built-in pneumatic micro-valve V2 was opened, the pressure of the pneumatic channel CH1 was adjusted, and Reg3 was driven to wash the cell.

The reagents Reg1-3 were injected into the chip in an orderly and gradient manner according to a predetermined design and reacted with the cell in the cell treating region 107 to meet the predetermined cell treating requirements. The flow rate control of the reagents Reg1-3 was the same as that in example 1.

In the process of cell treating, the operator could also pause and modify the treating parameters at any time according to a morphological observation result of the cell.

Step 5: Retrieving the Cell

The switching valves SV4 was switched to V6 position, the built-in pneumatic micro-valve V6 was closed, and the built-in pneumatic micro-valve V4 was opened. The switching valve SV3 was switched to the V5 position, and the built-in pneumatic micro-valve V5 was closed. The pressure of the pneumatic channel CH1 was adjusted, and the third reagent Reg3 was driven to travel along the third reagent inflow channel 1041 and the backwash channel 1042. At this time, the flow direction of Reg3 through the cell treating region 107 was changed from flowing from left to right in the fourth step to flowing from right to left, and the cell was further pushed into the cell retrieving hole.

Then, the input of Reg3 was stopped, and the subsequent gas flow completely removed the reagent liquid around the cell. After evacuating the reagent, the cell retrieving hole plug was opened, and the treated cell was extracted with a straw or a strip, as the cell carrier.

The invention claimed is:

1. A method of physicochemically treating a single cell using an automatic microfluidic device comprising a microfluidic chip and an optical fiber sensing module, the microfluidic chip comprising a fluidic layer, a pneumatic layer, an elastic layer sandwiched between the fluidic layer and the pneumatic layer, and a cell retrieving hole, the fluidic layer comprising a cell treating region and a cell retrieving channel, the cell retrieving hole connected with the cell retrieving channel, and the pneumatic layer comprising a pneumatic micro-valve group configured to control an opening and a closing of each channel in the fluidic layer, the method comprising:

sucking a single cell into the microfluidic chip by applying a negative pressure;

capturing the single cell in the cell treating region;

detecting a cell sensing signal with the optical fiber sensing module as a result of the single cell being captured in the cell treating region;

as a result of the optical fiber sensing module detecting the cell sensing signal when the single cell is captured in the cell treating region, physicochemically treating the single cell sequentially with a first reagent, then with a second reagent, and then with a third reagent, each reagent in different proportions, by controlling the pneumatic micro-valve group; and backwashing the single cell into the cell retrieving channel with the third reagent used to physicochemically treat the cell up until the single cell is captured at the cell retrieving hole;

if a residual volume of the third reagent after the backwashing exceeds 1 microliter, discharging the residual volume up until the residual volume does not exceed 1 microliter; and opening a plug of the cell retrieving hole, wherein the single cell is not subjected to damage during the physicochemical treatment.

2. A microfluidic chip usable to physicochemically treat a single cell without damaging the single cell, the microfluidic chip comprising a fluidic layer, a pneumatic layer, an elastic layer sandwiched between the fluidic layer and the pneumatic layer, and a cell retrieving hole, the fluidic layer comprising a cell treating region and a cell retrieving channel connected to the cell retrieving hole, the pneumatic layer comprising a pneumatic micro-valve group configured to control an opening and a closing of each channel in the fluidic layer, and the cell retrieving channel and the cell treating region having inner diameters larger than a diameter of the single cell to avoid damage to the single cell during use of the microfluidic chip.

3. The microfluidic chip according to claim 2, wherein:

the fluidic layer further comprises a switch-back single cell treating and retrieving channel, a first reagent inflow channel, a second reagent inflow channel, a reagent mixing channel, a third reagent inflow channel, a backwash channel, and a negative pressure and waste liquid sharing channel, the switch-back single cell treating and retrieving channel comprising the cell treating region and the cell retrieving channel; and the first reagent inflow channel and the second reagent inflow channel are separately connected with an inlet of the reagent mixing channel; wherein the reagent mixing channel, the third reagent inflow channel, the backwash channel, and the negative pressure and waste liquid sharing channel are separately connected with the switch-back single cell treating and retrieving channel; and wherein the third reagent inflow channel and the backwash channel are separately independent channels or comprise separately independent portions and a shared portion.

4. The microfluidic chip according to claim 3, wherein the switch-back single cell treating and retrieving channel further comprises a cell loading channel, wherein the cell loading channel and the cell retrieving channel are connected with the cell treating region at a same position upstream of the cell treating region, so that the single cell moves along the cell loading and cell retrieving channels in a switch-back manner in processes of cell loading, cell treating, and cell retrieving.

5. The microfluidic chip according to claim 4, wherein the cell loading channel is connected with a cell inlet for connecting with a cell loading device.

6. The automatic microfluidic chip according to claim 5, wherein the cell retrieving hole comprises a microwell placed at an end of the cell retrieving channel, wherein the microwell is a circular microhole whose vertical depth is deeper than or consistent with that of the cell retrieving channel.

7. The microfluidic chip according to claim 6, wherein the cell retrieving hole further comprises an annularly arranged micropillar array surrounding the microwell.

8. The microfluidic chip according to claim 3, wherein micropillar arrays are placed at connections between each of the reagent mixing channel, the third reagent inflow channel, the backwash channel, the negative pressure and waste liquid sharing channel, and the switch-back single cell treating and retrieving channel.

9. The microfluidic chip according to claim 8, wherein an arc-shape arranged micropillar array is placed at a connection between the cell treating region and the negative pressure and waste liquid sharing channel.

10. The microfluidic chip according to claim 3, wherein the negative pressure and waste liquid sharing channel is connected with an external negative pressure source in a process of cell loading and is connected with a waste liquid reservoir in processes of cell treating and cell retrieving.

11. The microfluidic chip according to claim 4, wherein: the pneumatic micro-valve group comprises first, second, and third pneumatic micro-valves, wherein inflows of the first reagent inflow channel, the second reagent inflow channel, and the reagent mixing channel are controlled by one first pneumatic micro-valve (V1);

the negative pressure and waste liquid sharing channel, the cell loading channel, and the cell retrieving channel are each controlled by one second pneumatic micro-valve (V5, V3, or V4); when the third reagent inflow channel and the backwash channel are separately independent channels, the third reagent inflow channel and the backwash channel are each controlled by one third pneumatic micro-valve (V2 or V6); and when the third reagent inflow channel and the backwash channel comprise the separately independent portions and the shared portion, one of the third pneumatic micro-valves (V2) controls inflow of a third reagent, and another one of the third pneumatic micro-valves (V6) realizes switching between forward-washing and backwashing of the cell treating region.

12. An automatic microfluidic device usable to physicochemically treat a single cell without damaging the single cell, the automatic microfluidic device comprising:

a microfluidic chip comprising a fluidic layer, a pneumatic layer, an elastic layer sandwiched between the fluidic layer and the pneumatic layer, and a cell retrieving hole, the fluidic layer comprising a cell treating region and a cell retrieving channel connected to the cell retrieving hole, the pneumatic layer comprising a pneumatic micro-valve group configured to control an opening and a closing of each channel in the fluidic layer, and the cell retrieving channel and the cell treating region having inner diameters larger than a diameter of the single cell to avoid damage to the single cell during operation of the automatic microfluidic device;
an optical fiber sensing module;
an air pressure generation and tuning module; and
a logic controlling circuit.

13. The automatic microfluidic device according to claim 12, wherein:
the optical fiber sensing module comprises an optical fiber head and an optical fiber amplifier, the optical fiber sensing module usable to monitor a position of the single cell;
the logic controlling circuit is usable to judge whether the single cell reaches a designated position by reading a cell sensing signal in real-time and then to judge whether to execute a next operation step; and
the air pressure generation and tuning module is usable to generate a negative pressure to suck the single cell into the microfluidic chip.

14. The automatic microfluidic device according to claim 12, wherein:
the fluidic layer of the microfluidic chip further comprises a switch-back single cell treating and retrieving channel, a first reagent inflow channel, a second reagent inflow channel, a reagent mixing channel, a third reagent inflow channel, a backwash channel, and a negative pressure and waste liquid sharing channel, the switch-back single cell treating and retrieving channel comprising the cell treating region and the cell retrieving channel; and
the first reagent inflow channel and the second reagent inflow channel are separately connected with an inlet of the reagent mixing channel; wherein the reagent mixing channel, the third reagent inflow channel, the backwash channel, and the negative pressure and waste liquid sharing channel are separately connected with the switch-back single cell treating and retrieving channel; and
wherein the third reagent inflow channel and the backwash channel are separately independent channels or comprise separately independent portions and a shared portion.

15. The automatic microfluidic device according to claim 14, wherein:
the optical fiber sensing module comprises an optical fiber head and an optical fiber amplifier, the optical fiber sensing module usable to monitor a position of the single cell;
the logic controlling circuit is usable to judge whether the single cell reaches a designated position by reading a cell sensing signal in real-time and then to judge whether to execute a next operation step; and
the air pressure generation and tuning module is usable to generate a negative pressure to suck the single cell into the microfluidic chip.

16. The automatic microfluidic device according to claim 14, wherein the switch-back single cell treating and retrieving channel further comprises a cell loading channel, wherein the cell loading channel and the cell retrieving channel are connected with the cell treating region at a same position upstream of the cell treating region, so that the single cell moves along the cell loading and cell retrieving channels in a switch-back manner in processes of cell loading, cell treating, and cell retrieving.

17. The automatic microfluidic device according to claim 16, wherein the cell loading channel is connected with a cell inlet for connecting with a cell loading device.

18. The automatic microfluidic device according to claim 17, wherein:
the optical fiber sensing module comprises an optical fiber head and an optical fiber amplifier, the optical fiber sensing module usable to monitor a position of the single cell;
the logic controlling circuit is usable to judge whether the single cell reaches a designated position by reading a cell sensing signal in real-time and then to judge whether to execute a next operation step; and
the air pressure generation and tuning module is usable to generate a negative pressure to suck the single cell into the microfluidic chip.

* * * * *